United States Patent [19]
Scherer et al.

[11] Patent Number: 5,869,330
[45] Date of Patent: Feb. 9, 1999

[54] DNA ENCODING A NOVEL SERUM PROTEIN PRODUCED EXCLUSIVELY IN ADIPOCYTES

[75] Inventors: Philipp E. Scherer, Watertown; Harvey F. Lodish, Brookline, both of Mass.

[73] Assignee: Whitehead Institute for Biomedical Research, Cambridge, Mass.

[21] Appl. No.: 463,911

[22] Filed: Jun. 5, 1995

[51] Int. Cl.⁶ .................. C07H 21/04; C12N 15/63
[52] U.S. Cl. .................. 435/320.1; 536/23.5; 536/24.31; 536/24.33; 935/8; 935/9; 935/21
[58] Field of Search .................. 424/130.1; 435/6, 435/91.2; 536/23.1, 24.31, 24.33, 23.5; 935/8, 9, 21

[56] References Cited

U.S. PATENT DOCUMENTS 5,223,425 6/1993 Flier et al. .................. 435/240.2

OTHER PUBLICATIONS

Kitagawa, K., et al., "Insulin stimulates the acute release of adipsin from 3T3–L1 adipocytes", *Biochimica et Biophysica Acta*, 1014:83–89 (1989).
Baldini, G., et al., "Cloning of a Rab3 isotype predominately expressed in adipocytes", *Proc. Natl. Acad. Sci. USA*, 89:5049–5052 (1992).
Spiegelman, B.M., et al., "Molecular Cloning of mRNA from 3T3 Adipocytes", *J. of Biol. Chem.*, 258(16):10083–10089 (1983).
Rink, T.J., "In search of a satiety factor", *Nature*, 372:406–407 (1994).
Zhang, Y., et al., "Positional cloning of the mouse obese gene and its human homologue", *Nature*, 372:425–432 (1994).
Kondo, N. and Kondo, J., "Identification of Novel Blood Proteins Specific for Mammalian Hibernation", *J. of Biol. Chem.*, 267(1):473–478 (1992).
Scherer, P.E., et al., "A Novel Serum Protein Similar to C1q, produced Exclusively in Adipocytes", *Journal of Biological Chemistry*, 270:26746–26749 (1995).
Maeda, K., et al., cDNA Cloning and Expression of a Novel Adipose Specific Collagen–like Factor, apM1 (Adipose Most Abundant Gene Transcript 1), *Biochemical & Biophysical Research Communications*, 221:286–289 (1996).
EMBL, accession No. D45371, Sequence Reference g871886, Jun. 28, 1995, Human apM1 mRNA for GS3109.
EMBL, accession No. U37222, Sequence Reference g1051267, Nov. 7, 1995, Mus musculus 30 kDa adipocyte complement–related protein Acrp30 mRNA.
EMBL, accession No. S23297, Sequence Reference S22243, Oct. 7, 1994, chicken mRNA complement C1q carboxy–terminal homology.
Maeda et al., Genbank Sequence Listing, 1995.

*Primary Examiner*—Carla J. Myers
*Attorney, Agent, or Firm*—Hamilton, Brook, Smith & Reynolds, P.C.

[57] ABSTRACT

The present invention relates to DNA encoding Acrp30, of vertebrate (e.g., mammalian) origin, and particularly of human and rodent origin. The present invention further relates to isolated, recombinantly produced or synthetic DNA which hybridizes to the nucleotide sequences described herein and RNA transcribed from the nucleotides sequence described herein. In addition, the invention relates to expression vectors comprising DNA encoding Acrp30, which is expressed when the vector is present in an appropriate host cell. The invention further relates to isolated, recombinantly produced or synthetic mammalian Acrp30 of vertebrate (e.g., mammalian) origin, and particularly of human and rodent origin. Also encompassed by the present invention is an inhibitor or enhancer of Acrp30. The present invention further relates to a method of identifying inhibitors or enhancers of Acrp30. Isolation of Acrp30 makes it possible to detect Acrp30 or adipocytes in a sample (e.g., test sample). In addition, the present invention relates to a method of regulating the energy balance (e.g., nutritional status) of a mammal by administering to the mammal an inhibitor or enhancer of the Acrp30.

5 Claims, 8 Drawing Sheets

```
CTCTAAAGAT TGTCAGTGGA TCTGACGACA CCAAAAGGGC TCAGG ATG CTA CTG           54
                                                  Met Leu Leu
                                                    1

TTG CAA GCT CTC CTG TTC CTC TTA ATC CTG CCC AGT CAT GCC GAA GAT        102
Leu Gln Ala Leu Leu Phe Leu Leu Ile Leu Pro Ser His Ala Glu Asp
      5                   10                  15

GAC GTT ACT ACA ACT GAA GAG CTA GCT CCT GCT TTG GTC CCT CCA CCC        150
Asp Val Thr Thr Thr Glu Glu Leu Ala Pro Ala Leu Val Pro Pro Pro
 20                  25                  30                  35

AAG GGA ACT TGT GCA GGT TGG ATG GCA GGC ATC CCA GGA CAT CCT GGC        198
Lys Gly Thr Cys Ala Gly Trp Met Ala Gly Ile Pro Gly His Pro Gly
             40                  45                  50

CAC AAT GGC ACA CCA GGC CGT GAT GGC AGA GAT GGC ACT CCT GGA GAG        246
His Asn Gly Thr Pro Gly Arg Asp Gly Arg Asp Gly Thr Pro Gly Glu
                 55                  60                  65

AAG GGA GAG AAA GGA GAT GCA GGT CTT CTT GGT CCT AAG GGT GAG ACA        294
Lys Gly Glu Lys Gly Asp Ala Gly Leu Leu Gly Pro Lys Gly Glu Thr
         70                  75                  80

GGA GAT GTT GGA ATG ACA GGA GCT GAA GGG CCA CGG GGC TTC CCC GGA        342
Gly Asp Val Gly Met Thr Gly Ala Glu Gly Pro Arg Gly Phe Pro Gly
     85                  90                  95

ACC CCT GGC AGG AAA GGA GAG CCT GGA GAA GCC GCT TAT ATG TAT CGC        390
Thr Pro Gly Arg Lys Gly Glu Pro Gly Glu Ala Ala Tyr Met Tyr Arg
100                 105                 110                 115

TCA GCG TTC AGT GTG GGG CTG GAG ACC CGC GTC ACT GTT CCC AAT GTA        438
Ser Ala Phe Ser Val Gly Leu Glu Thr Arg Val Thr Val Pro Asn Val
                120                 125                 130

CCC ATT CGC TTT ACT AAG ATC TTC TAC AAC CAA CAG AAT CAT TAT GAC        486
Pro Ile Arg Phe Thr Lys Ile Phe Tyr Asn Gln Gln Asn His Tyr Asp
            135                 140                 145

GGC AGC ACT GGC AAG TTC TAC TGC AAC ATT CCG GGA CTC TAC TAC TTC        534
Gly Ser Thr Gly Lys Phe Tyr Cys Asn Ile Pro Gly Leu Tyr Tyr Phe
        150                 155                 160

TCT TAC CAC ATC ACG GTG TAC ATG AAA GAT GTG AAG GTG AGC CTC TTC        582
Ser Tyr His Ile Thr Val Tyr Met Lys Asp Val Lys Val Ser Leu Phe
    165                 170                 175

AAG AAG GAC AAG GCC GTT CTC TTC ACC TAC GAC CAG TAT CAG GAA AAG        630
Lys Lys Asp Lys Ala Val Leu Phe Thr Tyr Asp Gln Tyr Gln Glu Lys
180                 185                 190                 195

AAT GTG GAC CAG GCC TCT GGC TCT GTG CTC CTC CAT CTG GAG GTG GGA        678
Asn Val Asp Gln Ala Ser Gly Ser Val Leu Leu His Leu Glu Val Gly
                200                 205                 210

GAC CAA GTC TGG CTC CAG GTG TAT GGG GAT GGG GAC CAC AAT GGA CTC        726
Asp Gln Val Trp Leu Gln Val Tyr Gly Asp Gly Asp His Asn Gly Leu
            215                 220                 225

TAT GCA GAT AAC GTC AAC GAC TCT ACA TTT ACT GGC TTT CTT CTC TAC        774
Tyr Ala Asp Asn Val Asn Asp Ser Thr Phe Thr Gly Phe Leu Leu Tyr
        230                 235                 240
```

FIGURE 1A

```
CAT GAT ACC AAC TGACTGCAAC TACCCATAGC CCATACACCA GGAGAATCAT      826
His Asp Thr Asn
    245

GGAACAGTCG ACACACTTTC AGCTTAGTTT GAGAGATTGA TTTTATTGCT TAGTTTGAGA  886

GTCCTGAGTA TTATCCACAC GTGTACTCAC TTGTTCATTA AACGACTTTA TAAAAAATAA  946

TTTGTGTTCC TAGTCCAGAA AAAAAGGCAC TCCCTGGTCT CCACGACTCT TACATGGTAG 1006

CAATAACAGA ATGAAAATCA CATTTGGTAT GGGGGCTTCA CAATATTCGC ATGACTGTCT 1066

GGAAGTAGAC CATGCTATTT TTCTGCTCAC TGTACACAAA TATTGTTCAC ATAAACCCTA 1126

TAATGTAAAT ATGAAATACA GTGATTACTC TTCTCACAGG CTGAGTGTAT GAATGTCTAA 1186

AGACCCATAA GTATTAAAGT GGTAGGGATA AATTGGAAAA AAAAAAAAA  AAAAAGAAAA 1246

ACTTTAGAGC ACACTGGCGG CCGTTACTAG                                 1276
```

```
AGGTCGACGG TATCGATAAG CTTGATATCG AATTCCGGCT GCGGTTCTGA TTCCATACCA         60

GAGGGGCTCA GG ATG CTG TTG CTG GGA GCT GTT CTA CTG CTA TTA GCT           108
      Met Leu Leu Leu Gly Ala Val Leu Leu Leu Leu Ala
       1               5                  10

CTG CCC GGT CAT GAC CAG GAA ACC ACG ACT CAA GGG CCC GGA GTC CTG         156
Leu Pro Gly His Asp Gln Glu Thr Thr Thr Gln Gly Pro Gly Val Leu
        15                  20                  25

CTT CCC CTG CCC AAG GGG GCC TGC ACA GGC TGG ATG GCG GGC ATC CCA         204
Leu Pro Leu Pro Lys Gly Ala Cys Thr Gly Trp Met Ala Gly Ile Pro
    30                  35                  40

GGG CAT CCG GGC CAT AAT GGG GCC CCA GGC CGT GAT GGC AGA GAT GGC         252
Gly His Pro Gly His Asn Gly Ala Pro Gly Arg Asp Gly Arg Asp Gly
 45                 50                  55                  60

ACC CCT GGT GAG AAG GGT GAG AAA GGA GAT CCA GGT CTT ATT GGT CCT         300
Thr Pro Gly Glu Lys Gly Glu Lys Gly Asp Pro Gly Leu Ile Gly Pro
                65                  70                  75

AAG GGA GAC ATC GGT GAA ACC GGA GTA CCC GGG GCT GAA GGT CCC CGA         348
Lys Gly Asp Ile Gly Glu Thr Gly Val Pro Gly Ala Glu Gly Pro Arg
            80                  85                  90

GGC TTT CCG GGA ATC CAA GGC AGG AAA GGA GAA CCT GGA GAA GGT GCC         396
Gly Phe Pro Gly Ile Gln Gly Arg Lys Gly Glu Pro Gly Glu Gly Ala
        95                 100                 105

TAT GTA TAC CGC TCA GCA TTC AGT GTG GGA TTG GAG ACT TAC GTT ACT         444
Tyr Val Tyr Arg Ser Ala Phe Ser Val Gly Leu Glu Thr Tyr Val Thr
    110                 115                 120

ATC CCC AAC ATG CCC ATT CGC TTT ACC AAG ATC TTC TAC AAT CAG CAA         492
Ile Pro Asn Met Pro Ile Arg Phe Thr Lys Ile Phe Tyr Asn Gln Gln
125                 130                 135                 140

AAC CAC TAT GAT GGC TCC ACT GGT AAA TTC CAC TGC AAC ATT CCT GGG         540
Asn His Tyr Asp Gly Ser Thr Gly Lys Phe His Cys Asn Ile Pro Gly
                145                 150                 155

CTG TAC TAC TTT GCC TAC CAC ATC ACA GTC TAT ATG AAG GAT GTG AAG         588
Leu Tyr Tyr Phe Ala Tyr His Ile Thr Val Tyr Met Lys Asp Val Lys
            160                 165                 170

GTC AGC CTC TTC AAG AAG GAC AAG GCT ATG CTC TTC ACC TAT GAT CAG         636
Val Ser Leu Phe Lys Lys Asp Lys Ala Met Leu Phe Thr Tyr Asp Gln
        175                 180                 185

TAC CAG GAA AAT AAT GTG GAC CAG GCC TCC GGC TCT GTG CTC CTG CAT         684
Tyr Gln Glu Asn Asn Val Asp Gln Ala Ser Gly Ser Val Leu Leu His
    190                 195                 200

CTG GAG GTG GGC GAC CAA GTC TGG CTC CAG GTG TAT GGG GAA GGA GAG         732
Leu Glu Val Gly Asp Gln Val Trp Leu Gln Val Tyr Gly Glu Gly Glu
205                 210                 215                 220

CGT AAT GGA CTC TAT GCT GAT AAT GAC AAT GAC TCC ACC TTC ACA GGC         780
Arg Asn Gly Leu Tyr Ala Asp Asn Asp Asn Asp Ser Thr Phe Thr Gly
                225                 230                 235

TTT CTT CTC TAC CAT GAC ACC AAC TGATCACCAC TAACTCAGAG CCTCCTCCAG        834
Phe Leu Leu Tyr His Asp Thr Asn
                240
```

FIGURE 5A

```
GCCAAACAGC CCCAAAGTCA ATTAAAGGCT TTCAGTACGG TTAGGAAGTT GATTATTATT      894

TAGTTGGAGG CCTTTAGATA TTATTCATTC ATTTACTCAT TCATTTATTC ATTCATTCAT      954

CAAGTAACTT TAAAAAAATC ATATGCTATG TTCCCAGTCC TGGGGAGCTT CACAAACATG     1014

ACCAGATAAC TGACTAGAAA GAAGTAGTTG ACAGTGCTAT TTCGTGCCCA CTGTCTCTCC     1074

TGATGCTCAT ATCAATCCTA TAAGGCACAG GGAACAAGCA TTCTCCTGTT TTTACAGATT     1134

GTATCCTGAG GCTGAGAGAG TTAAGTGAAT GTCTAAGGTC ACACAGTATT AAGTGACAGT     1194

GCTAGAAATC AAACCCAGAG CTGTGGACTT TGTTCACTAG ACTGTGCCCC TTTTATAGAG     1254

GGTACATGTT CTCTTTGGAG TGTTGGTAGG TGTCTGTTTC CCACCTCACC TGAGAGCCA     1313
```

FIGURE 5B

ACRP30: A COMPARISON OF MOUSE AND HUMAN VERSIONS

```
  1  M L L L Q A L L F L L T L P S H A E D D V T T T E E L A P A L V P P P K G T C A G W M A G I P G H P   Mouse
  1  M L L L G A V L L L L L L T L P G H — D Q E — T T T Q G P G V L L P L P K G A C T G W M A G I P G H P   Human 51  G H N G T P G R D G R D G R D G A P G E K G E K G D A G L L G P K G E T G D V G M T G A E G P R G F P G T   Mouse
 48  G H N G A P G R D G R D G T P G E K G E K G D P G L I G P K G D T G E T G V P G A E G P R G F P G T       Human 101  P G R K G E P G E A A Y M Y R S A F S V G L E T R V T V P N V P I R F T K I F Y N Q Q N H Y D G S T       Mouse
 98  Q G R K G E P G E G A Y V Y R S A F S V G L E T Y V T I P N M P I R F T K I F Y N Q Q N H Y D G S T       Human 151  G K F Y C N I P G L Y Y F S Y H I T V Y M K D V K V S L F K K D K A V L F T Y D Q Y Q E K N V D Q A       Mouse
148  G K F H C N I P G L Y Y F A Y H I T V Y M K D V K V S L F K K D K A M L F T Y D Q Y Q E N V D Q A         Human 201  S G S V L L H L E V G D Q V W L Q V Y G D H N G L Y A D N V N D S T F T G F L L Y H D T N                 Mouse
198  S G S V L L H L E V G D Q V W L Q V Y G E G E R N G L Y A D N D N D S T F T G F L L Y H D T N             Human
```

FIGURE 6

DNA ENCODING A NOVEL SERUM PROTEIN PRODUCED EXCLUSIVELY IN ADIPOCYTES

BACKGROUND OF THE INVENTION

Fat cells or adipocytes are a principal storage depot for triglycerides, and are thought to be endocrine cells. Adipocytes are the only cell type known to secrete the ob gene product and adipsin, which is equivalent to Factor D of the alternative complement pathway (Zhang, Y., et al., Nature 425–432 (1994); Spiegelman, B. M., et al., *J. Biol. Chem.* 258:10083–9 (1983)). The ob gene product is believed to be involved in the signalling pathway from adipose tissue that acts to regulate the size of the body fat depot. Mice homozygous for a defect in the ob gene become morbidly obese (for a review see Rink, T., *Nature*, 372:(1994)). However, little else is known about fat storage mechanisms or energy balance regulation.

A greater understanding of genes involved in regulating fat storage in an organism will provide new approaches for the treatment of a variety of conditions involving the energy balance and/or nutritional status of a host, such as obesity, obesity related disorders and anorexia.

SUMMARY OF THE INVENTION

The present invention is based on the discovery and isolation of a gene encoding a 30 kD protein produced exclusively in adipocytes. As shown herein, the protein, which is designated adipocyte complement related protein (Acrp30), is secreted by adipocytes and insulin enhances this secretion. Evidence provided herein indicates that Acrp30 is involved in the energy balance (e.g., the nutritional status) of a vertebrate (e.g., a mammal).

The present invention relates to DNA encoding Acrp30, of vertebrate (e.g., mammalian) origin, and particularly of human and rodent origin. The DNA of the present invention can be isolated or purified from natural sources, recombinantly produced or chemically synthesized. The DNA of the present invention includes DNA encoding murine Acrp30 (SEQ ID NO:1), DNA encoding human Acrp30 (SEQ ID NO:6), DNA encoding other vertebrate Acrp30 and portions thereof which either encode vertebrate Acrp30 or identify nucleotide sequences which encode Acrp30 (e.g., a nucleic acid probe). The invention also relates to complementary sequences (i.e., a complement) of SEQ ID NO:1, SEQ ID NO:6 and portions thereof.

The present invention further relates to isolated, recombinantly produced or synthetic DNA which hybridizes to the nucleotide sequences described herein and encodes Acrp30 (i.e., a protein having the same amino acid sequence or encodes a protein with the same characteristics of Acrp30). In particular, the invention relates to DNA which hybridizes to SEQ ID No: 1, SEQ ID No: 6, other sequences which encode vertebrate Acrp30 or portions thereof. RNA transcribed from DNA having the nucleotide sequence of SEQ ID No: 1, a complementary sequence of SEQ ID NO:1, SEQ ID No: 6, a complementary sequence of SEQ ID NO:6 or portions thereof are also encompassed by the present invention.

In addition, the invention relates to expression vectors comprising DNA encoding Acrp30, which is expressed when the vector is present in an appropriate host cell. In particular, the expression vector of the present invention comprises the nucleotide sequence of SEQ ID No: 1, SEQ ID No: 6 or portions thereof.

The invention further relates to isolated, recombinantly produced or synthetic Acrp30 of vertebrate (e.g., mammalian) origin, and particularly of human and rodent origin. The Acrp30 of the present invention has the amino acid sequence of SEQ ID No: 2, the amino acid sequence of SEQ ID No: 7, an amino acid sequence of other vertebrate Acrp30, or portions thereof which have the same characteristics as Acrp30 as described herein.

Also encompassed by the present invention is an agent which interacts with Acrp30 directly or indirectly, and inhibits or enhances Acrp30 function. In one embodiment, the agent is an inhibitor which interferes with Acrp30 directly (e.g., by binding Acrp30) or indirectly (e.g., by blocking the ability of Acrp30 to interact with or bind a molecule which it normally interacts with or binds in order to function). In a particular embodiment, the inhibitor is an antibody specific for Acrp30 or a portion of Acrp30 protein; that is, the antibody binds the Acrp30 protein. For example, the antibody can be specific for the protein encoded by the amino acid sequence of rodent Acrp30 (SEQ ID No: 2), the amino acid sequence of human Acrp30 (SEQ ID No: 7) or portions thereof. Alternatively, the inhibitor can be an agent other than an antibody (e.g., small organic molecule, protein, peptide) which binds Acrp30 and blocks its activity. For example, the inhibitor can be an agent which mimics Acrp30 structurally but lacks its function. Alternatively, it can be an agent which binds or interacts with a molecule which Acrp30 normally binds or interacts with, thus blocking Acrp30 from doing so and preventing it from exerting the effects it would normally exert. In another embodiment, the agent is an enhancer of Acrp30 which increases the activity of Acrp30 (increases the effect of a given amount or level of Acrp30), increases the length of time it is effective (by preventing its degradation or otherwise prolonging the time during which it is active) or both either directly or indirectly.

The present invention further relates to a method of identifying inhibitors or enhancers of Acrp30. An inhibitor of Acrp30 interferes with the function or bioactivity of Acrp30, directly or indirectly. An enhancer of Acrp30 enhances the function or bioactivity of Acrp30, also directly or indirectly.

Isolation of Acrp30 makes it possible to detect Acrp30 or adipocytes in a sample (e.g., test sample). In the method of the present invention, the sample is treated to render nucleic acids in the sample available for hybridization to a nucleic acid probe. In one embodiment, the nucleic acids in the sample are combined with a labeled nucleic acid probe having all or a portion of the nucleotide sequence of mammalian Acrp30, under conditions appropriate for hybridization of complementary nucleic acid sequences to occur. For example, the nucleic acid probe comprises the nucleotide sequence of SEQ ID No: 1, the complement of SEQ ID NO:1, SEQ ID No: 6, the complement of SEQ ID NO:6, or portions thereof. Specific hybridization of a sequence in the treated sample with the labeled nucleic acid probe indicates that mammalian Acrp30 and/or adipocytes are present in the sample. The method of detecting mammalian Acrp30 in the sample can also be accomplished by combining the sample with an antibody directed against all or a portion of mammalian Acrp30 and detecting specific binding of the antibody in the sample. The occurrence of specific binding of the antibody indicates the presence of Acrp30 in the sample. An antibody directed against Acrp30 can also be used to detect the presence of adipocytes in a primary cell culture line.

In addition, the present invention relates to a method of regulating the energy balance (e.g., nutritional status) of a mammal, by administering to the mammal, an agent (e.g., an inhibitor or an enhancer of the Acrp30) which interacts with Acrp30, either directly or indirectly. This method can be used to decrease weight gain in a mammal (e.g., for conditions related to obesity) or conversely, to increase weight gain in a mammal (e.g., for conditions related to anorexia)

The data presented herein supports a role for Acrp30 protein as a factor in the system of energy balance or homeostasis involving food intake, and carbohydrate and lipid catabolism and anabolism. Thus, the ability to modify or control the expression and activity of Acrp30 allows for methods of altering the energy balance (e.g., nutritional status) of a vertebrate, particularly a mammal such as a human. In particular, the present invention allows for treatment of a variety of conditions involving the energy balance (e.g., nutritional status, lipid deposition) of a host (e.g., vertebrate, particularly mammal such as a human), such as obesity, obesity related disorders and anorexia.

BRIEF DESCRIPTION OF THE FIGURES

FIG. 1 is the nucleotide sequence (SEQ. ID NO: 1) and amino acid sequence (SEQ ID NO:2) of murine Acrp30.

FIG. 3 is an alignment of the amino acid sequences of Acrp30 (SEQ ID No: 2), Hib27 (SEQ ID No: 3), C1q-C (SEQ ID No: 4) and the globular domain of the type X collagen (SEQ ID No: 5).

FIG. 5 is the nucleotide sequence (SEQ ID NO: 6) and amino acid sequence (SEQ ID NO: 7) of human Acrp30.

FIG. 6 is a comparison of the amino acid sequence of the mouse Acrp30 (SEQ ID No: 2) and the amino acid sequence of the human Acrp30 (SEQ ID No: 7).

DETAILED DESCRIPTION OF THE INVENTION

Figure 2:
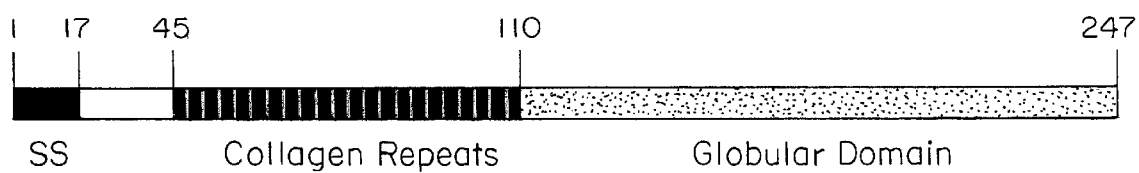
FIG. 2 is an illustration of the predicted structure of the Acrp30.

The present invention is based on the discovery of a novel 30 kD secretory protein, termed adipocyte complement related protein (Acrp30), which is made exclusively in adipocytes. Adipocytes also secrete tumor necrosis factor α, (TNFα), complement factors C3 and B (Hotamisligil, G. S., et al., *Science* 250:87–91 (1993); Flier, J. S., et al., *Science* 237:405–8 (1987), adipsin and the ob gene product.

Acrp30 is structurally similar to complement factor C1q and to a hibernation-specific protein isolated from the plasma of Siberian chipmunks. Acrp30 is an abundant serum protein and, like adipsin, secretion of Acrp30 is enhanced by insulin. The data provided herein shows that, like the ob protein, Acrp30 is a factor that is involved in the control of the energy balance (e.g., energy metabolism, nutritional state, lipid storage) of a vertebrate (e.g., mammal). Thus, Acrp30 participates in the delicately balanced system of energy homeostasis involving food intake and carbohydrate and lipid catabolism. Experiments described herein further corroborate the existence of an insulin-regulated secretory pathway for adipocytes.

The subject invention relates to DNA encoding Acrp30 of vertebrate (e.g., mammalian) origin, particularly rodent and human origin. The DNA of the present invention includes DNA encoding murine Acrp30 (SEQ ID NO:1), DNA encoding human Acrp30 (SEQ ID NO:6), DNA encoding other vertebrate Acrp30 and portions thereof which either encode vertebrate Acrp30 or identify nucleotide sequences which encode Acrp30 (e.g., a nucleic acid probe). In another embodiment, the invention relates to a complementary sequence of SEQ ID NO:1, a complementary sequence of SEQ ID NO:6 and portions thereof.

Identification of Acrp30 makes it possible to isolate DNA encoding Acrp30 from other vertebrate organisms (e.g., monkey, pig) using nucleic acid probes which hybridize to all or a portion of the nucleotide sequences described herein and known hybridization methods. For example, as described in Example 5, the murine Acrp30 nucleotide sequence was used to produce a probe for isolation of the human homologue of Acrp30 using a hybridization method. Such nucleic acids can be detected and isolated under high stringency conditions or moderate stringency conditions, for example. "High stringency conditions" and "moderate stringency conditions" for nucleic acid hybridizations are explained on pages 2.10.1–2.10.16 (see particularly 2.10.8–11) and pages 6.3.1–6 in *Current Protocols in Molecular Biology* (Ausubel, F. M. et al., eds., Vol. 1, Suppl. 26, 1991), the teachings of which are hereby incorporated by reference. Factors such as probe length, base composition, percent mismatch between the hybridizing sequences, temperature and ionic strength influence the stability of nucleic acid hybrids. Thus, high or moderate stringency conditions can be determined empirically, depending in part upon the characteristics of the known DNA to which other unknown nucleic acids are being compared for sequence similarity. See Maniatis et al., *Molecular Cloning, A Laboratory Manual,* 2d, Cold Spring Harbor Press (1989) which is incorporated herein by reference.

The invention also includes products encoded by the DNA described herein. In one embodiment, the invention relates to RNA transcribed from the nucleotide sequences of Acrp30.

In another embodiment, the invention relates to Acrp30 encoded by the nucleotide sequences described herein. The present invention relates to isolated, recombinantly produced or synthetic (e.g., chemically synthesized) Acrp30 of vertebrate origin (e.g., mammalian), particularly of rodent and human origin. The Acrp30 of the present invention has the amino acid sequence of SEQ ID No: 2, the amino acid sequence of SEQ ID No: 7, the amino acid sequence which encodes other vertebrate Acrp30 and portions thereof which encode Acrp30.

This invention includes portions of the above mentioned DNA, RNA and proteins. As used herein, "portion" refers to portions of sequences, proteins and substances of sufficient size or sequence to have the function or activity of Acrp30 involved in the nutritional status of the organism or mammal (e.g., a protein that is expressed by adipocytes, inhibits enhanced secretion by insulin, and is present in normal serum). In addition, the terms include a nucleotide sequence which, through the degeneracy of the genetic code, encodes the same peptide as a peptide whose sequence is presented herein (SEQ ID NO:2, SEQ ID NO:7). The nucleic acid or protein described herein may also contain a modification of the molecule such that the resulting gene produced is sufficiently similar to that encoded by the unmodified sequence that it has essentially the same activity. An example of such a modification would be a "silent" codon or amino acid substitution, for instance, from one acidic amino acid to another acidic amino acid, or from one codon encoding a hydrophobic amino acid to another codon encoding a hydrophobic amino acid. See Ausubel, F. M. et al., *Current Protocols in Molecular Biology,* Greene Publ. Assoc. and Wiley-Interscience 1989.

The claimed DNA, RNA and proteins described herein refer to substantially pure or isolated nucleic acids and proteins, which can be isolated or purified from natural, vertebrate sources, particularly mammalian (e.g., human, murine) sources, using the sequences described herein and known methods. In addition, the claimed DNA, RNA and proteins of the present invention can be obtained by genetic engineering (i.e., are recombinantly produced) or by chemical synthesis using the sequences described herein and known methods.

The present invention also relates to expression vectors comprising the nucleotide sequences described herein. In particular embodiments, the expression vectors of the present invention comprise DNA having the nucleotide sequence of SEQ ID NO: 1, SEQ ID NO: 6 or portions thereof. The construction of expression vectors can be accomplished using known genetic engineering techniques or by using commercially available kits. (See, e.g., Sambrook, J., et al., *Molecular Cloning* 2nd Ed. Cold Spring Harbor Press, 1989; Ausubel, F. M., et al., *Current Protocols In Molecular Biology*, Green Publishing Assoc. and Wiley-Interscience, 1988).

Also encompassed by the present invention is an agent which interacts with Acrp30 directly or indirectly. In one embodiment, the agent is an inhibitor of Acrp30. Inhibitors of Acrp30 include substances which inhibit expression, function or activity of Acrp30 directly or indirectly (e.g., expression by adipocytes, enhanced secretion by insulin and presence in serum). The embodiment which encompasses inhibitors of Acrp30 includes antibodies directed against or which bind to Acrp30 including portions of antibodies, which can specifically recognize and bind to Acrp30. The term "antibody" includes polyclonal and monoclonal antibodies, as well as single chain antibodies, chimeric or humanized antibodies. The antibody preparations include antibodies which are monospecific for mammalian, particularly human and murine, Acrp30. Preparation of antibody can be performed using the encoded protein of this invention and any suitable procedure. A variety of methods are described in the following publications, the teachings of which are incorporated by reference (Harlow, E., et al., *Antibodies: A Laboratory Manual*, Cold Spring Harbor Laboratory Press, 1988; Huse, W. D., et al., *Journal of Science* 246:1275–1281 (1989); Moore, J. P., *Journal of Clinical Chemistry* 35:1849–1853 (1989) Kohler et al., *Nature*, 256:495–497 (1975) and *Eur. J. Immunol.* 6:511–519 (1976); Milstein et al., *Nature* 266:550–552 (1977); Koprowski et al., U.S. Pat. No. 4,172,124; Harlow, E. and D. Lane, 1988, *Antibodies: A Laboratory Manual*, (Cold Spring Harbor Laboratory: Cold Spring Harbor, N.Y.); *Current Protocols In Molecular Biology*, Vol. 2 (Supplement 27, Summer '94), Ausubel, F. M. et al., Eds., (John Wiley & Sons: New York, N.Y.), Chapter 11, (1991)).

Alternatively, an inhibitor can be an agent other than an antibody (e.g., small organic molecule, protein, peptide) which binds Acrp30 and directly blocks its activity. The inhibitor can be an agent which mimics Acrp30 structurally but lacks its function; or can be an agent which binds or interacts with a molecule which Acrp30 normally binds or interacts with, thus blocking Acrp30 from doing so and preventing it from exerting the effects it would normally exert. An inhibitor of Acrp30 can be a substance which inhibits the expression of Acrp30 by adipocytes or the ability of insulin to enhance the secretion of Acrp30 from adipocytes.

In another embodiment, the agent is an enhancer of Acrp30. An enhancer of Acrp30 is an agent which increases the activity of Acrp30 (increases the effect of a given amount or level of Acrp30), increases the length of time it is effective (by preventing its degradation or otherwise prolonging the time during which it is active) or both.

Enhancers of Acrp30 also include substances which enhance the expression, function or activity of Acrp30. For example, expression vectors comprising a nucleotide sequence encoding Acrp30 can be administered to a host to enhance expression of Acrp30 in the host. In addition, insulin can be administered to a host to increase the secretion of Acrp30 in the host.

The present invention also relates to a method of identifying a substance or agent which is an inhibitor or an enhancer of Acrp30. The agent to be assessed is combined with Acrp30 and a molecule (i.e., the molecule) which Acrp30 normally interacts with or binds. If Acrp30 is unable to interact with or bind the molecule in the presence of the agent when compared to a control test sample which does not contain the agent (i.e., a test sample containing Acrp30 and the molecule) then the agent is an inhibitor. Alternatively, if interaction with or binding of Acrp30 with the molecule is increased or enhanced in the presence of the agent to be assessed when compared to a control test sample, then the agent is an enhancer of Acrp30.

Several expression vectors for use in making the constructs described herein and administering Acrp30 to a host are available commercially or can be produced using known recombinant DNA and cell culture techniques. For example, vector systems such as retroviral, yeast or vaccinia virus expression systems, or virus vectors can be used in the methods and compositions of the present invention (Kaufman, R. J., *J. of Method. in Cell. and Molec. Biol.*, 2:221–236 (1990)). Other techniques using naked plasmids of DNA, and cloned genes encapsidated in liposomes or in erythrocyte ghosts, can be used to introduce the constructs of the present invention into a host (Freidman, T., *Science*, 244:1275–1281 (1990); Rabinovich, N. R. et al., *Science*, 265:1401–1404 (1994)).

The Acrp30 nucleic acids (DNA, RNA) and protein products of the present invention can be used in a variety of ways. In one embodiment, the sequences described herein can be used to detect Acrp30 in a sample. For example, a labeled nucleic acid probe having all or a functional portion of the nucleotide sequence of mammalian Acrp30 can be used in a method to detect mammalian Acrp30 in a sample. In one embodiment, the sample is treated to render nucleic acids in the sample available for hybridization to a nucleic acid probe. The resulting treated sample is combined with a labeled nucleic acid probe having all or a portion of the nucleotide sequence of mammalian Acrp30, under conditions appropriate for hybridization of complementary sequences to occur. Detection of hybridization of the sample with the labeled nucleic acid probe indicates the presence of mammalian Acrp30 in a sample. In addition, this embodiment provides a means of identifying adipocytes in a sample. As described herein, Acrp30 is produced exclusively in adipocytes. Thus, detecting the presence of Acrp30 in a sample using this embodiment is also an indication that the sample contains adipocytes.

Alternatively, a method of detecting mammalian Acrp30 in a sample can be accomplished using an antibody directed against Acrp30 or a portion of mammalian Acrp30. Detection of specific binding to the antibody indicates the presence of mammalian Acrp30 in the sample (e.g., ELISA). This could reflect a pathological state associated with Acrp30.

In addition, an antibody directed against Acrp30 can be used to determine the presence of adipocytes in a primary culture cell line. For example, a primary culture cell line derived from a tissue sample is cultured in appropriate cell culture medium. A sample of conditioned culture medium (i.e., medium which has been exposed to the cells of the primary culture for a period of time) can be removed and tested for the presence of Acrp30 using an antibody directed against Acrp30. Detection of specific binding of the antibody indicates the presence of Acrp30 in the conditioned culture medium, which indicates that adipocytes are present in the primary cell culture line.

The sample for use in the methods of the present invention includes a suitable sample from a vertebrate (e.g., mammal, particularly human). For example, the sample can be blood, urine, lymph or tissue from a mammal.

The present invention also relates to a method of regulating or altering the energy balance (e.g., nutritional status, lipid deposition) of a host (e.g., mammal) by administering to the host an agent which interacts with Acrp30 directly or indirectly. For example, in the instance in which weight loss is desired (e.g., obesity), an inhibitor or an enhancer of Acrp30 (e.g., an antibody which binds to Acrp30) can be administered to a mammal to control weight gain in the mammal. In the instance in which weight gain is desired (e.g., anorexia), an inhibitor or enhancer of Acrp30 (e.g., insulin, expression vectors comprising nucleotide sequences encoding Acrp30) can be administered to a mammal to enhance weight gain in the mammal.

Figure 3:
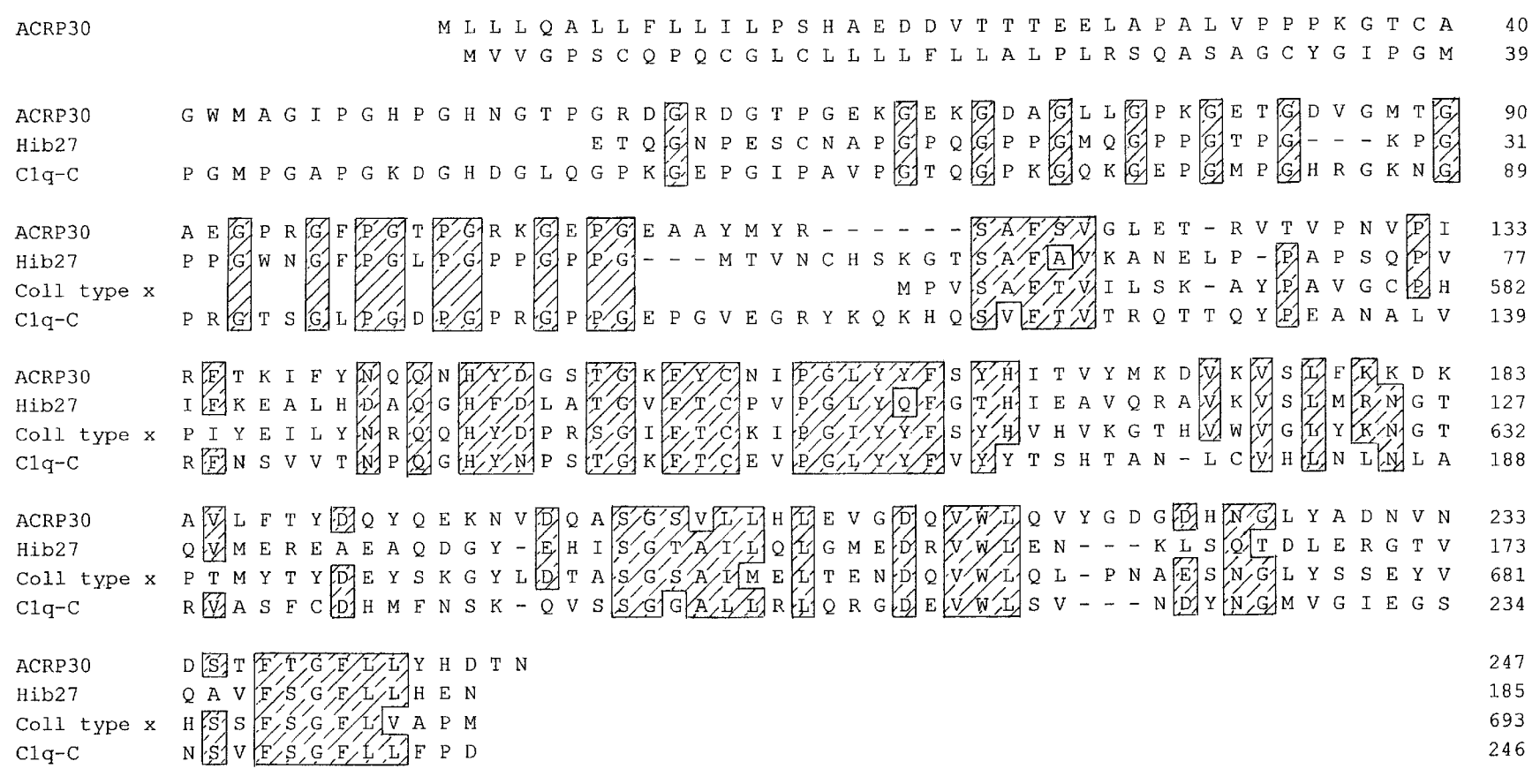

The following is a description of the isolation and characterization of Acrp30. As described in Example 1, in order to identify novel adipocyte-specific proteins, portions of 1000 clones from a subtractive cDNA library enriched in mRNAs induced during adipocyte differentiation of 3T3-L1 fibroblasts were randomly sequenced. Northern blot analysis using one ~250 bp clone showed a marked induction during adipocyte differentiation and thus a full-length cDNA was isolated and sequenced. The encoded protein, Acrp30, is novel; it contains 247 amino acids with a predicted molecular weight of 28 kD. Acrp30 consists of a predicted amino-terminal signal sequence, followed by a stretch of 27 amino acids that does not show any significant homology and then by 22 perfect GlyXPro or GlyXX repeats (FIGS. 1 and 2). As shown in FIG. 3, the carboxy-terminal globular domain exhibits striking homology to a number of proteins, such as the globular domains of type VIII and type X collagens (i.e., coll type x) (Reichenberger, E., et al., *Febs. Lett.*, 311:305–10 (1992)), the subunits of complement factor C1q (i.e., C1q.c) (Reid, K. B., et al., *Biochem. J.,* 203:559–69 (1982)) and a protein found in the serum of hibernating animals during the summer months (i.e., Hib27) (Kondo, N. & Kondo, J., *J. Biol. Chem.,* 267:473–8 (1992)). Structurally, albeit not at the primary sequence level, the protein resembles the lung surfactant protein (Floros, J., et al., *J. Biol. Chem.,* 261:9029–33 (1986)) and the hepatocyte mannan-binding protein (Drickamer, K., et al., *J. Biol. Chem.,* 261:6878–87 (1986)), both of which have collagen-like domains and globular domains of similar size.

Northern blot analysis shows that Acrp30 is expressed exclusively in adipocytes (see Example 1). It is not expressed in 3T3-L1 fibroblasts, and is induced over 100-fold during adipocyte differentiation. Induction occurs between days 2 and 4, at the same time as other adipocyte-specific proteins such as GLUT4 (Charron, M. J., et al., *Proc. Natl. Acad. Sci. USA,* 86:2535–9 (1989)) and Rab3D (Baldini, G., et al., *Proc. Natl. Acad. Sci. USA,* 89:5049–52 (1992)).

As described in Example 2, an antibody raised against a peptide corresponding to the unique amino-terminal domain of Acrp30 recognized a 3T3-L1 adipocyte protein of approximately 28 kD. Acrp30 contains one potential N-glycosylation site, within the collagen domain, but apparently is not glycosylated; Endo H treatment did not cause a shift in molecular weight of Acrp30 at any time during a metabolic pulse-chase experiment. Acrp30 does become modified posttranslationally, since after 20 min. of chase there was a small but reproducible reduction in gel mobility. This most likely represents hydroxylation of collagen-domain proline residues in the endoplasmic reticulum or Golgi compartments, by analogy to a similar modification in the structurally related mannan-binding protein (MBP) (Colley, K. J. and Baenziger, J. U., *J. Biol. Chem.,* 262:10290–5 (1987)). In 3T3-L1 adipocytes unstimulated by insulin, 50% of newly-made Acrp30 is secreted into the medium at 2.5 to 3 hours of chase. Indeed, Acrp30 can be detected by Western blotting in normal mouse serum. The antipeptide antibody is specific for the mouse homologue, as it does not cross-react with bovine, human or rabbit serum.

Insulin causes translocation of several receptor proteins from intracellular membranes to the plasma membrane (Corvera, S., et al., *J. Biol. Chem.,* 264:10133–8 (1989); Davis, R. J., et al., *J. Biol. Chem.,* 261:8708–11 (1986). Adipocytes are highly responsive to insulin and translocate intracellular glucose transporters to the cell surface upon stimulation with insulin (Simpson, I. A. & Cushman, S. W., *Ann. Rev. Biochem.,* 55:1059–89 (1986); Wardzala, L. J., et al., *J. Biol. Chem.,* 259:8378–83 (1984)), and also causes a two-fold stimulation of adipsin secretion (Kitagawa, K., et al., *Biochim. Biophys. Acta.,* 1014:83–9 (1989)). For example, insulin stimulation of adipocytes causes exocytosis of intracellular vesicles containing the GLUT4 glucose transporter and a concomitant increase in glucose uptake. As described in the pulse chase experiment of Example 3, during the first 60 minutes of chase, insulin causes a four-fold increase in secretion of newly-made Acrp30. After 60 minutes the rates of Acrp30 secretion are the same in unstimulated and insulin-stimulated cells. Similarly, insulin causes a four-fold increase in adipsin secretion during the first 30 minutes of chase, but afterwards the rate of adipsin secretion is the same in control and insulin-treated cells. See FIG. 4. (Kitagawa, K., et al., *Biochim. Biophys. Acta.,* 1014:83–9 (1989)). It is reasonable to expect that a fraction of newly-made adipsin and Acrp30 are sorted, probably in the trans-Golgi reticulum, into regulated secretory vesicles whose exocytosis is induced by insulin whereas the balance is sorted into vesicles that are constitutively exocytosed. Partial sorting of protein hormones into regulated secretory vesicles has been seen in other types of cultured cells (Moore, H.-P. H., et al., *Nature,* 302:434–436 (1983); Sambanis, A., Stephanopoulos, G., et al., *Biotech. Bioeng.,* 35:771–780 (1990)).

Complement factor C1q consists of three related polypeptides that form heterotrimeric subunits containing a three-stranded collagen "tail" and three globular "heads"; six of these subunits generate an eighteen-mer complex often referred to as a "bouquet of flowers." The experiments described in Example 4 show that Acrp30 has a similar oligomeric structure, but is composed of a single type of polypeptide chain. When analyzed by velocity gradient sedimentation analysis, Acrp30 in blood serum migrates as two species of apparent molecular weights 90 kDa and 300 kDa. Disregarding the presumably non-globular shape of the complex that could lead to a slight distortion of the molecular weight determination, the former is probably a trimer and the latter could be a nonamer or dodecamer.

Isoelectric focusing followed by SDS-PAGE of [$^{35}$S] Acrp30 secreted by 3T3-L1 adipocytes reveals only a single polypeptide, suggesting that Acrp30 forms homo-oligomeric structures. Chemical crosslinking using low concentrations of $BS^3$ of [$^{35}S$] medium from 3T3-L1 adipocytes, followed by specific immunoprecipitation and SDS-PAGE under reducing conditions, shows mainly dimers and trimers. Larger concentrations of the $BS^3$ cross-linking agent generated Acrp30 proteins that migrated as hexamers as well as yet larger species. As extensively cross-linked proteins migrate aberrantly upon SDS-PAGE, it is difficult to determine the exact size of the high molecular weight form indicated by an asterisk. It could represent either a nonamer or a dodecameric structure. Results show that Acrp30 forms homotrimers that interact together to generate nonamers or dodecamers. Non-reducing SDS-PAGE reveals that two of the subunits in a trimer are disulfide-bonded together, similar to other proteins containing a collagen domain, including the macrophage scavenger receptor (Resnick, D., et al., *J. Biol. Chem.*, 268:3538–3545 (1993)). Besides being a homo-oligomer, Acrp30 differs from C1q in containing an uninterrupted stretch of 22 perfect GlyXX repeats; this suggests that Acrp30 has a straight collagen stalk as opposed to the characteristic kinked collagen domain in C1q caused by imperfect GlyXX repeats in two of the three subunits (reviewed in (Thiel, S. and Reid, K. B., *Febs. Lett.*, 250:78–84 (1989)).

The human Acrp30 protein was isolated through the use of a probe derived from the mouse Acrp30 nucleotide sequence, and sequenced, as described in Example 5. Comparison of the mouse Acrp30 amino acid sequence with the human Acrp30 amino acid sequence showed that 82% homology exists between the two sequences and that the highest degree of sequence divergence occurs near the N-terminus of the mouse and the human Acrp30 sequence.

Acrp30 is a relatively abundant serum protein, accounting for up to 0.05% of total serum protein as judged by quantitative Western blotting using recombinant ACRP30 as a standard. Possibly Acrp30, like C3 complement released by adipocytes, is converted proteolytically to a bioactive molecule.

The experiments described herein corroborate the existence of a regulated secretory pathway in adipocytes. Whether adipsin and/or Acrp30 are in the same intracellular vesicles that contain GLUT4 and that fuse with the plasma membrane in response to insulin, or whether they are in different types of vesicles is not yet known. Adipocytes express two members of the Rab3 family, Rab3A and Rab3D (Baldini, G., et al., *Proc. Natl. Acad. Sci. USA* (1995)). These are found in vesicles of different density. Rab3's are small GTP-binding proteins involved in regulated exocytic events. Except for adipocytes Rab3A is found only in neuronal and neuroendocrine cells; in neurons Rab3A is localized to synaptic vesicles and is important for their targeting to the plasma membrane. An attractive hypothesis under test is that in adipocytes Rab3A is localized to vesicles containing Acrp30 and/or adipsin, and that possibly Rab3D mediates insulin-triggered exocytosis of vesicles containing GLUT4. In any case, the mechanism of signal transduction from the insulin receptor to regulated exocytosis of intracellular vesicles remains an important unsolved problem.

Thus, since the coding sequence of a novel serum protein which is involved in the regulatory pathway of adipocytes has been determined, compositions (e.g., nucleotide sequences, protein, expression vectors and inhibitors), methods of detecting Acrp30 and methods of inhibiting the activity of Acrp30 using all or portions of the Acrp30 DNA or encoded product (e.g., protein, RNA) are within the scope of the present invention.

The invention is further illustrated in the following examples, which are not intended to be limiting.

EXEMPLIFICATION

EXAMPLE 1

Isolation and Sequencing of the Murine Acrp30 Protein

A full-length cDNA library templated by mRNA from 3T3-L1 adipocytes at day 8 of differentiation (Baldini, G., et al., *Proc. Natl. Acad. Sci. USA*, 89:5049–52 (1992)) was screened with a digoxygenin-labeled cDNA fragment obtained from the random sequencing screen. Labeling, hybridization, and detection were performed according to the manufacturer's instructions (Boehringer Inc.). One of he positive clones obtained was subjected to automated sequencing on an Applied Biosystems 373-A sequencer. The entire 1.3 kb insert was sequenced at least 2 independent times on one stand and once on the complementary strand. Sequence analysis was performed with the DNAstar package and showed an open reading frame of 741 bp encoding a protein of 28 kD. Homology searches were performed at NCBI using the BLAST network service, and alignments were performed with the Megalign program from DNAstar using the Clustal algorithm. Only the globular domain for the type X collagen was used for the alignment (residues 562–680).

FIG. 2 is the predicted structure of murine Acrp30. The protein consists of an amino-terminal signal sequence (SS) followed by a sequence of 27 amino acids lacking significant homologies to any entries in the Genbank database. A peptide corresponding to part of this sequence, was used to generate specific anti-Acrp30 antibodies (MAP technology, Research Genetics). This region is followed by a stretch of 22 collagen repeats with 7 "perfect" Gly-X-Pro repeats (dark hatched boxes) clustered at the beginning and end of the domain interspersed with 15 "imperfect" Gly-X-Y repeats (light hatched boxes). The C-terminal 138 amino acids probably form a globular domain.

FIG. 3 shows the alignment of the amino acid sequences of Acrp30 (SEQ ID NO: 2); Hib27 (SEQ ID NO: 3), a member of the hibernation-specific protein family; C1q-C (SEQ ID NO: 4), one of the subunits of complement C1q; and the globular domain of the type X collagen (SEQ ID NO: 5). Conserved residues are shaded. For simplicity, the other members of each family are not shown, but shaded conserved residues are in most instances conserved within each protein family.

Northern Blot Analysis of Acrp30 Expression

Isolation of mRNA from tissues and from 3T3-L1 cells at various stages of differentiation was as described in (Baldini, G., et al., *Proc. Natl. Acad. Sci. USA*, 89:5049–52 (1992)), as was [$^{35}P$] labeling of DNA, agarose gel electrophoresis of mRNA, and its transfer to nylon membranes. Hybridizations were performed overnight at 42° C. in 50% formamide, 5× SSC, 25 mM Na-phosphate pH 7.0, 10× Denhardt's solution, 5 mM EDTA, 1% SDS, and 0.1 mg/ml PolyA; the [$^{35}P$] DNA probes were used at concentrations of $2 \times 10^6$ cpm/ml. The filters were subsequently washed in 2× SSC/0.1% SDS and 0.1× SSC/0.1% SDS at 50° C. The same filters were thereafter stripped and reprobed with a probe encoding one of the constitutively expressed cytosolic hsp70s. Autoradiography was for 4 hours (Acrp30) and 24 hours (hsp70).

Northern blot analysis of Acrp30 expression in murine cells from kidney, liver, brain, testis, fat, (adipocytes) diaphragm, heart, lung, spleen and cultured 3T3-L1 adipocytes was carried out. PolyA-RNA isolated from various tissues was probed with the full-length Acrp30 cDNA. The predominant Acrp30 mRNA is 1.4 kb and was shown to be expressed only in adipose tissue and cultured 3T3-L1 adipocytes. Overexposure of the autoradiogram did not reveal expression in any other tissue.

Induction of the Acrp30 message during differentiation of 3T3-L1 fibroblasts to adipocytes was assessed. Induction of Acrp30 occurs primarily between days 2 and 4 of differentiation, the same time at which induction of the insulin receptor and the insulin-responsive glucose transporter GLUT4 occurs.

EXAMPLE 2

Acrp30 is a Secretory Protein Found in Blood

Ten 6 cm diameter dishes of 3T3-L1 adipocytes were starved for 30 min. in Dulbecco's modified Eagle medium (DME, ICN, Costa Mesa), lacking cysteine and methionine and then labeled for 10 min. in the same medium containing 0.5 mCi/ml of Express Protein Labeling Reagent (1000 Ci/mmol) [NEN (Boston, Mass.)]. The cells were then washed twice with DME supplemented with unlabeled cysteine and methionine and then fresh growth medium containing 300 µM cycloheximide was added. At each of the indicated time points the medium from one plate was collected and the cells washed with ice-cold PBS and then lysed in lysis buffer (1% Triton X-100, 60 mM octylglucoside, 150 mM NaCl, 20 mM Tris pH 8.0, 2 mM EDTA, 1 mM PMSF, and 2 µg/ml leupeptin). Insoluble material from both the medium and cell lysate was removed by centrifugation (15,000 g for 10 min.); the supernatants were precleared with 50 µl Protein A-Sepharose for 30 min. at 4° C. and then immunoprecipitated with 50 µl of affinity-purified anti-Acrp30 antibody for 2 hrs. at 4° C. Immunoprecipitates were washed 4 times in lysis buffer lacking octylglucoside and once in PBS, then resuspended in Endo H buffer (0.1M Na-citrate pH 6.0, 1% SDS), boiled for 5 min., and intracellular samples were incubated for 2 hrs. either in absence (−) or presence (+) of 1000 U Endo H (New England Biolabs) at 37° C. Reactions were stopped by boiling in 2× sample buffer (250 mM Tris pH 6.8, 4 mM EDTA, 4% SDS, 20% sucrose) and analyzed by electrophoresis through a 12% polyacrylamide gel containing SDS. Mr: Molecular weight marker. Labeled proteins were visualized by fluorography.

An antibody raised against a peptide corresponding to the unique amino-terminal domain of Acrp30 recognized a 3T3-L1 adipocyte protein of approximately 28 kD. Acrp30 contains one potential N-glycosylation site, within the collagen domain, but apparently is not glycosylated; Endo H treatment did not cause a shift in molecular weight of Acrp30 at any time during a metabolic pulse-chase experiment. Acrp30 does become modified posttranslationally, since after 20 min. of chase there was a small but reproducible reduction in gel mobility. This most likely represents hydroxylation of collagen-domain proline residues in the endoplasmic reticulum or Golgi compartments, by analogy to a similar modification in the structurally related mammalian-binding protein (MBP) (Colley, K. J. and Baenziger, J. U., *J. Biol. Chem.*, 262:10290–5 (1987)). In 3T3-L1 adipocytes unstimulated by insulin, 50% of newly-made Acrp30 is secreted into the medium at 2.5 to 3 hours of chase.

Western Blot Analysis

One microliter of fetal calf, rabbit, mouse and human serum was boiled for 5 min. in 2× sample buffer and analyzed by SDS-PAGE and Western blotting with the anti-Acrp30 antibody according to standard protocols. Antibody was visualized with an anti-rabbit IgG antibody coupled to horseradish peroxidase using a chemiluminescence kit from New England Nuclear Corporation, Boston.

Results showed that Acrp30 was detected by Western blotting in serum from mice; the antibody does not cross-react with calf, human or rabbit serum.

EXAMPLE 3

Insulin Stimulation of Acrp30 and Adipsin Secretion by 3T3-L1 Adipocytes

Two 10 cm dishes of 3T3-L1 adipocytes on the 8th day after differentiation were labeled for 10 min. in medium containing [$^{35}$S] methionine and cysteine as described in Example 2. The cells were then incubated in growth medium containing cycloheximide and containing or lacking 100 nM insulin. Every 30 min. the culture medium was removed and replaced with fresh, prewarmed medium containing or lacking 100 nM insulin. The media were subjected to sequential immunoprecipitations with anti-Acrp30 and anti-adipsin antibodies as described in Example 2 and analyzed by electrophoresis through a 12% polyacrylamide gel containing SDS. Acrp30 and adipsin contain a comparable number of cysteine and methionine residues (7 and 9, respectively) and equal exposures of the autoradiograms were used. Therefore, one can determine from the intensities of the bands resulting from the 12% polyacrylamide gel containing SDS that approximately equal amounts of the two proteins are secreted. As judged by the amount of [$^{35}$S] proteins remaining in the cells after the 2 hr. chase, all of the [$^{35}$S] adipsin and about 40% of the [$^{35}$S] Acrp30 has been secreted at this time.

Figure 4:
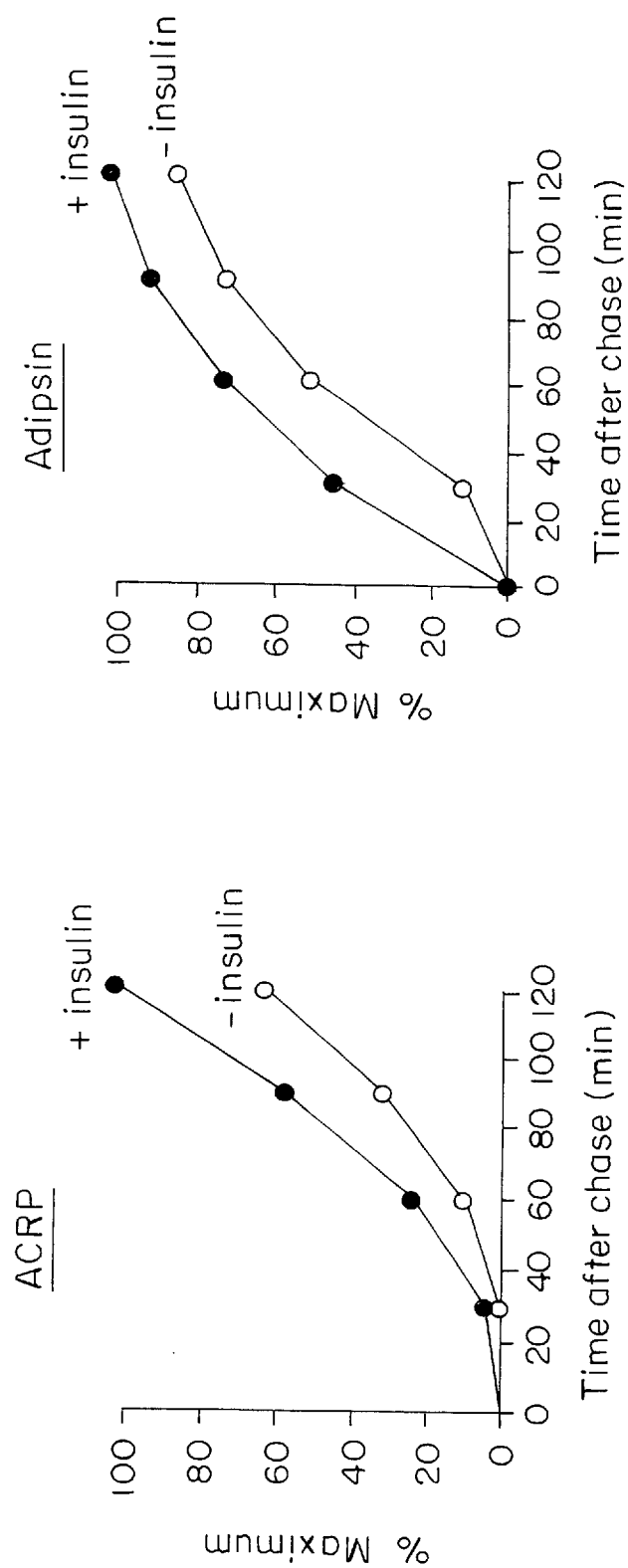
FIG. 4 are graphs of time versus % Acrp30 or adipsin protein secreted by 3T3-L1 adipocytes in the presence (closed squares) and absence (open squares) of insulin.

The autoradiograms were scanned in a Molecular Dynamics densitometer, and the cumulative amount secreted at each time point was plotted. The amount of each protein secreted after 120 min. in the presence of insulin was taken as 100%. FIG. 4 shows quantitation of Acrp30 and Adipsin secretion by 3T3-L1 adipocytes in the presence (closed squares) and absence (open circles) of insulin.

EXAMPLE 4

Oligomeric Structure of Acrp30

One 10 cm plate of 3T3-L1 adipocytes on the 8th day after differentiation was labeled overnight with [$^{35}$S] methionine and cysteine as described in Example 2. The medium was collected and, by means of several spins in a Centricon 10 microconcentrator, the buffer was replaced with 150 mM NaCl, 50 mM KP$_i$, pH 8.5. A stock solution of 200 mg/ml Bis (sulfosuccinimidyl) suberate (BS$^3$; Pierce Inc.) in dimethylsulfoxide was prepared and added to the indicated final concentrations. Reactions were allowed to proceed for 30 min. on ice and excess crosslinker was quenched by addition of 500 mM Tris buffer, pH 8.0. Samples were diluted 1:1 with lysis buffer and subjected to immunoprecipitation with anti-Acrp30 antibodies. Immunoprecipitates were analyzed by gradient SDS-PAGE (7–12.5% acrylamide) followed by fluorography. In the lane "Total" 1% of the amount of cell medium used for the crosslinking reactions was analyzed on the same gel; a comparison of the "Total" lane and lane 1 demonstrates the specificity of the antibody used for immunoprecipitation. Rainbow markers (Amersham) together with a Phosphorylase b ladder (Sigma) were used as molecular weight markers.

[$^{35}$S] labeled 3T3-L1 culture supernatant was incubated with increasing amounts of the BS$^3$ crosslinking reagent and immunoprecipitated with Acrp30-specific antibodies. The results revealed a set of crosslinked products whose molecular sizes are multiples of 30 kDa. Predominant species are trimers, hexamers and a high molecular weight species (asterisk) that could correspond to a nonamer or a dodecamer.

Medium from 3T3-L1 adipocytes on the 8th day after differentiation labeled overnight with [$^{35}$S] methionine and cysteine was immunoprecipitated with anti-Acrp30 antibodies as described in Example 2. Half of the sample was subjected to SDS-PAGE (7–12.5% acrylamide gradient) in the presence (reducing) or absence (non-reducing) of 50 mM DTT. Labeled proteins were detected by fluorography.

One microliter of mouse serum was diluted with 50 μl PBS and layered on top of a 4.5 ml. linear 5–20% sucrose gradient in PBS and centrifuged for 10 hrs. at 60,000 rpm in a SW60 rotor of a Beckman ultracentrifuge. Thirteen 340 μl fractions were collected from the top and analyzed by SDS-PAGE and Western blotting using anti-Acrp30 antibodies. An identical gradient was run in parallel with a set of molecular weight standards: cytochrome c (14 kD), carbonic anhydrase (29 kD), bovine serum albumin (68 kD), alcohol dehydrogenase (150 kD), β-amylase (200 kD), and apoferritin (443 kD). Results show that Acrp30 forms homotrimers that interact together to generate nonamers or dodecamers. Non-reducing SDS-PAGE reveals that two of the subunits in a trimer are disulfide-bonded together, similar to other proteins containing a collagen domain, including the macrophage scavenger receptor (Resnick, D., et al., *J. Biol. Chem.*, 268:3538–3545 (1993)).

Velocity gradient centrifugation of mouse serum displays two discrete Acrp30-immunoreactive species. The smallest corresponds to a trimer of Acrp30 polypeptides and the larger a nonamer or dodecamer.

EXAMPLE 5

Isolation and Sequencing of the Human Acrp30 Protein

The sequencing and isolation of the human Acrp30 protein was performed using methods similar to those described in Example 1. The nucleotide sequence of human Acrp30 is shown in FIG. 5. FIG. 6 illustrates a comparison of the mouse and human Acrp30 sequences.

Southern Blot Analysis

The complete mouse cDNA was used as a probe for a low stringency hybridization on genomic DNA from a number of different species: mouse, human, Drosophila and Xenopus samples were tested. Crosshybridizing bands were detected in the human sample; no signal was seen in the Drosophila and Xenopus samples. The mouse cDNA probe was labeled according to standard methods. The probe was used at 2×10$^6$ cpm/ml. Hybridizations were performed overnight at 42° in 30% formamide, 5×SSC, 25 mM Na-phosphate pH 7.0, 10× Denhardt's solution, 5 mM EDTA, 1% SDS, and 0.1 mg/ml PolyA. The filters were subsequently washed in 2× SSC/ 0.1% SDS at 50° C.

Isolation of Clone

The conditions established for Southern blot analysis were used to screen for the human homolog. [A reduction of 20% formamide during the hybridization (30% instead of the standard 50% in high stringency hybridizations) translates into a reduction of 14° C. in the hybridization temperature in aqueous buffers]. Therefore, colony hybridization was performed at 50° C. using the digoxygenin-labeled mouse cDNA fragment. Washes were done with 2× SSC/ 0.1% SDS at 50° C. All other buffers and incubations, including labeling of the mouse probe with digoxigenin and detection of positive plaques were performed as described for the isolation of the mouse clone according to the manufacturer's instructions (Boehringer Inc.). A commercially available library was used for the isolation of the human clone; a human fat cell 5'-Stretch Plus cDNA library (sold by Clonetech Inc., Article #HL3016b) was used. The mRNA source for this library was abdominal fat from a Caucasian female. A total of 5×10$^4$ plaques were screened and several positive clones were isolated. For one of the positive clones obtained, a series of Exonuclease III deletions was generated. These deletions were subjected to automated sequencing on an Applied Biosystems 373-A sequencer. Human Acrp30 is 82% similar to its mouse counterpart with the highest degree of sequence divergence located near the N-terminus.

EQUIVALENTS

Those skilled in the art will recognize, or be able to ascertain using no more than routine experimentation, many equivalents to the specific embodiments of the invention described specifically herein. Such equivalents are intended to be encompassed in the scope of the following claims.

We claim:

1. Isolated or recombinantly produced polynucleotide comprising a nucleotide sequence selected from the group consisting of: SEQ ID NO: 1 and SEQ ID NO: 6.

2. Isolated polynucleotide comprising a nucleotide sequence selected from the group consisting of:

a) a DNA sequence which encodes Acrp30 and hybridizes under conditions of low stringency to a probe having the sequence of the full length complement of the coding sequence of SEQ ID No: 1; and b) a DNA sequence which encodes Acrp30 and hybridizes under conditions of low stringency to a probe having the sequence of the full length complement of the coding sequence of SEQ ID NO: 6.

3. Isolated polynucleotide encoding a protein, wherein the protein comprises an amino acid sequence selected from the group consisting of SEQ ID NO:2, and SEQ ID NO:7.

4. Isolated RNA transcribed from DNA comprising a nucleotide sequence selected from the group consisting of SEQ ID NO:1 and SEQ ID NO:6.

5. An expression vector comprising DNA selected from the group consisting of: SEQ ID NO: 1 and SEQ ID NO: 6.

* * * * *

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 1276 base pairs
        ( B ) TYPE: nucleic acid
        ( C ) STRANDEDNESS: single
        ( D ) TOPOLOGY: linear (  i i  ) MOLECULE TYPE: DNA (genomic)

(  i x  ) FEATURE:
    ( A ) NAME/KEY: CDS
    ( B ) LOCATION: 46..786

(  x i  ) SEQUENCE DESCRIPTION: SEQ ID NO:1:

```
CTCTAAAGAT TGTCAGTGGA TCTGACGACA CCAAAGGGC TCAGG ATG CTA CTG                54
                                                   Met Leu Leu
                                                    1

TTG CAA GCT CTC CTG TTC CTC TTA ATC CTG CCC AGT CAT GCC GAA GAT           102
Leu Gln Ala Leu Leu Phe Leu Leu Ile Leu Pro Ser His Ala Glu Asp
     5              10              15

GAC GTT ACT ACA ACT GAA GAG CTA GCT CCT GCT TTG GTC CCT CCA CCC           150
Asp Val Thr Thr Thr Glu Glu Leu Ala Pro Ala Leu Val Pro Pro Pro
 20              25              30                          35

AAG GGA ACT TGT GCA GGT TGG ATG GCA GGC ATC CCA GGA CAT CCT GGC           198
Lys Gly Thr Cys Ala Gly Trp Met Ala Gly Ile Pro Gly His Pro Gly
                 40              45                       50

CAC AAT GGC ACA CCA GGC CGT GAT GGC AGA GAT GGC ACT CCT GGA GAG           246
His Asn Gly Thr Pro Gly Arg Asp Gly Arg Asp Gly Thr Pro Gly Glu
             55              60                      65

AAG GGA GAG AAA GGA GAT GCA GGT CTT CTT GGT CCT AAG GGT GAG ACA           294
Lys Gly Glu Lys Gly Asp Ala Gly Leu Leu Gly Pro Lys Gly Glu Thr
         70              75                  80

GGA GAT GTT GGA ATG ACA GGA GCT GAA GGG CCA CGG GGC TTC CCC GGA           342
Gly Asp Val Gly Met Thr Gly Ala Glu Gly Pro Arg Gly Phe Pro Gly
     85              90                  95

ACC CCT GGC AGG AAA GGA GAG CCT GGA GAA GCC GCT TAT ATG TAT CGC           390
Thr Pro Gly Arg Lys Gly Glu Pro Gly Glu Ala Ala Tyr Met Tyr Arg
100             105             110                         115

TCA GCG TTC AGT GTG GGG CTG GAG ACC CGC GTC ACT GTT CCC AAT GTA           438
Ser Ala Phe Ser Val Gly Leu Glu Thr Arg Val Thr Val Pro Asn Val
                 120             125                     130

CCC ATT CGC TTT ACT AAG ATC TTC TAC AAC CAA CAG AAT CAT TAT GAC           486
Pro Ile Arg Phe Thr Lys Ile Phe Tyr Asn Gln Gln Asn His Tyr Asp
             135             140                     145

GGC AGC ACT GGC AAG TTC TAC TGC AAC ATT CCG GGA CTC TAC TAC TTC           534
Gly Ser Thr Gly Lys Phe Tyr Cys Asn Ile Pro Gly Leu Tyr Tyr Phe
         150             155                 160

TCT TAC CAC ATC ACG GTG TAC ATG AAA GAT GTG AAG GTG AGC CTC TTC           582
Ser Tyr His Ile Thr Val Tyr Met Lys Asp Val Lys Val Ser Leu Phe
     165             170                 175

AAG AAG GAC AAG GCC GTT CTC TTC ACC TAC GAC CAG TAT CAG GAA AAG           630
Lys Lys Asp Lys Ala Val Leu Phe Thr Tyr Asp Gln Tyr Gln Glu Lys
180             185             190                         195

AAT GTG GAC CAG GCC TCT GGC TCT GTG CTC CAT CTG GAG GTG GGA                678
Asn Val Asp Gln Ala Ser Gly Ser Val Leu His Leu Glu Val Gly
                 200             205                     210

GAC CAA GTC TGG CTC CAG GTG TAT GGG GAT GGG GAC CAC AAT GGA CTC           726
Asp Gln Val Trp Leu Gln Val Tyr Gly Asp Gly Asp His Asn Gly Leu
             215             220                     225

TAT GCA GAT AAC GTC AAC GAC TCT ACA TTT ACT GGC TTT CTT CTC TAC           774
Tyr Ala Asp Asn Val Asn Asp Ser Thr Phe Thr Gly Phe Leu Leu Tyr
         230             235                 240

CAT GAT ACC AAC TGACTGCAAC TACCCATAGC CCATACACCA GGAGAATCAT              826
His Asp Thr Asn
         245

GGAACAGTCG ACACACTTTC AGCTTAGTTT GAGAGATTGA TTTTATTGCT TAGTTTGAGA         886

GTCCTGAGTA TTATCCACAC GTGTACTCAC TTGTTCATTA AACGACTTTA TAAAAATAA          946
```

```
TTTGTGTTCC  TAGTCCAGAA  AAAAAGGCAC  TCCCTGGTCT  CCACGACTCT  TACATGGTAG      1006

CAATAACAGA  ATGAAAATCA  CATTTGGTAT  GGGGGCTTCA  CAATATTCGC  ATGACTGTCT      1066

GGAAGTAGAC  CATGCTATTT  TTCTGCTCAC  TGTACACAAA  TATTGTTCAC  ATAAACCCTA      1126

TAATGTAAAT  ATGAAATACA  GTGATTACTC  TTCTCACAGG  CTGAGTGTAT  GAATGTCTAA      1186

AGACCCATAA  GTATTAAAGT  GGTAGGGATA  AATTGGAAAA  AAAAAAAAA   AAAAAGAAAA      1246

ACTTTAGAGC  ACACTGGCGG  CCGTTACTAG                                          1276
```

( 2 ) INFORMATION FOR SEQ ID NO:2:

( i ) SEQUENCE CHARACTERISTICS:
        ( A ) LENGTH: 247 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  Leu  Leu  Leu  Gln  Ala  Leu  Leu  Phe  Leu  Leu  Ile  Leu  Pro  Ser  His
 1                    5                        10                       15

Ala  Glu  Asp  Asp  Val  Thr  Thr  Thr  Glu  Leu  Ala  Pro  Ala  Leu  Val
               20                        25                   30

Pro  Pro  Pro  Lys  Gly  Thr  Cys  Ala  Gly  Trp  Met  Ala  Gly  Ile  Pro  Gly
               35                        40                        45

His  Pro  Gly  His  Asn  Gly  Thr  Pro  Gly  Arg  Asp  Gly  Arg  Asp  Gly  Thr
      50                        55                        60

Pro  Gly  Glu  Lys  Gly  Glu  Lys  Gly  Asp  Ala  Gly  Leu  Leu  Gly  Pro  Lys
65                        70                        75                       80

Gly  Glu  Thr  Gly  Asp  Val  Gly  Met  Thr  Gly  Ala  Glu  Gly  Pro  Arg  Gly
                    85                        90                        95

Phe  Pro  Gly  Thr  Pro  Gly  Arg  Lys  Gly  Glu  Pro  Gly  Glu  Ala  Ala  Tyr
                   100                       105                      110

Met  Tyr  Arg  Ser  Ala  Phe  Ser  Val  Gly  Leu  Glu  Thr  Arg  Val  Thr  Val
               115                       120                      125

Pro  Asn  Val  Pro  Ile  Arg  Phe  Thr  Lys  Ile  Phe  Tyr  Asn  Gln  Gln  Asn
          130                       135                      140

His  Tyr  Asp  Gly  Ser  Thr  Gly  Lys  Phe  Tyr  Cys  Asn  Ile  Pro  Gly  Leu
145                       150                       155                     160

Tyr  Tyr  Phe  Ser  Tyr  His  Ile  Thr  Val  Tyr  Met  Lys  Asp  Val  Lys  Val
                    165                       170                      175

Ser  Leu  Phe  Lys  Lys  Asp  Lys  Ala  Val  Leu  Phe  Thr  Tyr  Asp  Gln  Tyr
               180                       185                      190

Gln  Glu  Lys  Asn  Val  Asp  Gln  Ala  Ser  Gly  Ser  Val  Leu  Leu  His  Leu
          195                       200                      205

Glu  Val  Gly  Asp  Gln  Val  Trp  Leu  Gln  Val  Tyr  Gly  Asp  Gly  Asp  His
     210                       215                       220

Asn  Gly  Leu  Tyr  Ala  Asp  Asn  Val  Asn  Asp  Ser  Thr  Phe  Thr  Gly  Phe
225                      230                        235                      240

Leu  Leu  Tyr  His  Asp  Thr  Asn
                    245
```

( 2 ) INFORMATION FOR SEQ ID NO:3:

( i ) SEQUENCE CHARACTERISTICS:
        ( A ) LENGTH: 185 amino acids
        ( B ) TYPE: amino acid
        ( C ) STRANDEDNESS: single
        ( D ) TOPOLOGY: linear (ii) MOLECULE TYPE: DNA (genomic)

(xi) SEQUENCE DESCRIPTION: SEQ ID NO:3:

| Glu | Thr | Gln | Gly | Asn | Pro | Glu | Ser | Cys | Asn | Ala | Pro | Gly | Pro | Gln | Gly |
|---|---|---|---|---|---|---|---|---|---|---|---|---|---|---|---|
| 1 | | | | 5 | | | | | 10 | | | | | 15 | |

| Pro | Pro | Gly | Met | Gln | Gly | Pro | Pro | Gly | Thr | Pro | Gly | Lys | Pro | Gly | Pro |
|---|---|---|---|---|---|---|---|---|---|---|---|---|---|---|---|
| | | | 20 | | | | | 25 | | | | | 30 | | |

| Pro | Gly | Trp | Asn | Gly | Phe | Pro | Gly | Leu | Pro | Gly | Pro | Pro | Gly | Pro | Pro |
|---|---|---|---|---|---|---|---|---|---|---|---|---|---|---|---|
| | | 35 | | | | | 40 | | | | | 45 | | | |

| Gly | Met | Thr | Val | Asn | Cys | His | Ser | Lys | Gly | Thr | Ser | Ala | Phe | Ala | Val |
|---|---|---|---|---|---|---|---|---|---|---|---|---|---|---|---|
| | 50 | | | | | 55 | | | | | 60 | | | | |

| Lys | Ala | Asn | Glu | Leu | Pro | Pro | Ala | Pro | Ser | Gln | Pro | Val | Ile | Phe | Lys |
|---|---|---|---|---|---|---|---|---|---|---|---|---|---|---|---|
| 65 | | | | | 70 | | | | | 75 | | | | | 80 |

| Glu | Ala | Leu | His | Asp | Ala | Gln | Gly | His | Phe | Asp | Leu | Ala | Thr | Gly | Val |
|---|---|---|---|---|---|---|---|---|---|---|---|---|---|---|---|
| | | | | 85 | | | | | 90 | | | | | 95 | |

| Phe | Thr | Cys | Pro | Val | Pro | Gly | Leu | Tyr | Gln | Phe | Gly | Phe | His | Ile | Glu |
|---|---|---|---|---|---|---|---|---|---|---|---|---|---|---|---|
| | | | 100 | | | | | 105 | | | | | 110 | | |

| Ala | Val | Gln | Arg | Ala | Val | Lys | Val | Ser | Leu | Met | Arg | Asn | Gly | Thr | Gln |
|---|---|---|---|---|---|---|---|---|---|---|---|---|---|---|---|
| | | 115 | | | | | 120 | | | | | 125 | | | |

| Val | Met | Glu | Arg | Glu | Ala | Glu | Ala | Gln | Asp | Gly | Tyr | Glu | His | Ile | Ser |
|---|---|---|---|---|---|---|---|---|---|---|---|---|---|---|---|
| | 130 | | | | | 135 | | | | | 140 | | | | |

| Gly | Thr | Ala | Ile | Leu | Gln | Leu | Gly | Met | Glu | Asp | Arg | Val | Trp | Leu | Glu |
|---|---|---|---|---|---|---|---|---|---|---|---|---|---|---|---|
| 145 | | | | | 150 | | | | | 155 | | | | | 160 |

| Asn | Lys | Leu | Ser | Gln | Thr | Asp | Leu | Glu | Arg | Gly | Thr | Val | Gln | Ala | Val |
|---|---|---|---|---|---|---|---|---|---|---|---|---|---|---|---|
| | | | | 165 | | | | | 170 | | | | | 175 | |

| Phe | Ser | Gly | Phe | Leu | Ile | His | Glu | Asn | | | | | | | |
|---|---|---|---|---|---|---|---|---|---|---|---|---|---|---|---|
| | | | 180 | | | | | 185 | | | | | | | |

(2) INFORMATION FOR SEQ ID NO:4:

(i) SEQUENCE CHARACTERISTICS:
(A) LENGTH: 246 amino acids
(B) TYPE: amino acid
(C) STRANDEDNESS: single
(D) TOPOLOGY: linear (ii) MOLECULE TYPE: DNA (genomic)

(xi) SEQUENCE DESCRIPTION: SEQ ID NO:4:

| Met | Val | Val | Gly | Pro | Ser | Cys | Gln | Pro | Gln | Cys | Gly | Leu | Cys | Leu | Leu |
|---|---|---|---|---|---|---|---|---|---|---|---|---|---|---|---|
| 1 | | | | 5 | | | | | 10 | | | | | 15 | |

| Leu | Leu | Phe | Leu | Leu | Ala | Leu | Pro | Leu | Arg | Ser | Gln | Ala | Ser | Ala | Gly |
|---|---|---|---|---|---|---|---|---|---|---|---|---|---|---|---|
| | | | 20 | | | | | 25 | | | | | 30 | | |

| Cys | Tyr | Gly | Ile | Pro | Gly | Met | Pro | Gly | Met | Pro | Gly | Ala | Pro | Gly | Lys |
|---|---|---|---|---|---|---|---|---|---|---|---|---|---|---|---|
| | | 35 | | | | | 40 | | | | | 45 | | | |

| Asp | Gly | His | Asp | Gly | Leu | Gln | Gly | Pro | Lys | Gly | Glu | Pro | Gly | Ile | Pro |
|---|---|---|---|---|---|---|---|---|---|---|---|---|---|---|---|
| | 50 | | | | | 55 | | | | | 60 | | | | |

| Ala | Val | Pro | Gly | Thr | Gln | Gly | Pro | Lys | Gly | Gln | Lys | Gly | Glu | Pro | Gly |
|---|---|---|---|---|---|---|---|---|---|---|---|---|---|---|---|
| 65 | | | | | 70 | | | | | 75 | | | | | 80 |

| Met | Pro | Gly | His | Arg | Gly | Lys | Asn | Gly | Pro | Arg | Gly | Thr | Ser | Gly | Leu |
|---|---|---|---|---|---|---|---|---|---|---|---|---|---|---|---|
| | | | | 85 | | | | | 90 | | | | | 95 | |

| Pro | Gly | Asp | Pro | Gly | Pro | Arg | Gly | Pro | Pro | Gly | Glu | Pro | Gly | Val | Glu |
|---|---|---|---|---|---|---|---|---|---|---|---|---|---|---|---|
| | | | 100 | | | | | 105 | | | | | 110 | | |

| Gly | Arg | Tyr | Lys | Gln | Lys | His | Gln | Ser | Val | Phe | Thr | Val | Thr | Arg | Gln |
|---|---|---|---|---|---|---|---|---|---|---|---|---|---|---|---|
| | | 115 | | | | | 120 | | | | | 125 | | | |

| Thr | Thr | Gln | Tyr | Pro | Glu | Ala | Asn | Ala | Leu | Val | Arg | Phe | Asn | Ser | Val |
|---|---|---|---|---|---|---|---|---|---|---|---|---|---|---|---|
| | 130 | | | | | 135 | | | | | 140 | | | | |

| | | | | | | | | | | | | | | | |
|---|---|---|---|---|---|---|---|---|---|---|---|---|---|---|---|
| Val | Thr | Asn | Pro | Gln | Gly | His | Tyr | Asn | Pro | Ser | Thr | Gly | Lys | Phe | Thr |
| 145 | | | | | 150 | | | | | 155 | | | | | 160 |
| Cys | Glu | Val | Pro | Gly | Leu | Tyr | Tyr | Phe | Val | Tyr | Tyr | Thr | Ser | His | Thr |
| | | | | 165 | | | | | 170 | | | | | 175 | |
| Ala | Asn | Leu | Cys | Val | His | Leu | Asn | Leu | Asn | Leu | Ala | Arg | Val | Ala | Ser |
| | | | 180 | | | | | 185 | | | | | 190 | | |
| Phe | Cys | Asp | His | Met | Phe | Asn | Ser | Lys | Gln | Val | Ser | Ser | Gly | Gly | Ala |
| | | 195 | | | | | 200 | | | | | 205 | | | |
| Leu | Leu | Arg | Leu | Gln | Arg | Gly | Asp | Glu | Val | Trp | Leu | Ser | Val | Asn | Asp |
| | 210 | | | | 215 | | | | | | 220 | | | | |
| Tyr | Asn | Gly | Met | Val | Gly | Ile | Glu | Gly | Ser | Asn | Ser | Val | Phe | Ser | Gly |
| 225 | | | | | 230 | | | | | 235 | | | | | 240 |
| Phe | Leu | Leu | Phe | Pro | Asp | | | | | | | | | | |
| | | | | 245 | | | | | | | | | | | |

( 2 ) INFORMATION FOR SEQ ID NO:5:

( i ) SEQUENCE CHARACTERISTICS:
        ( A ) LENGTH: 132 amino acids
        ( B ) TYPE: amino acid
        ( C ) STRANDEDNESS: single
        ( D ) TOPOLOGY: linear ( x i ) SEQUENCE DESCRIPTION: SEQ ID NO:5:

| | | | | | | | | | | | | | | | |
|---|---|---|---|---|---|---|---|---|---|---|---|---|---|---|---|
| Met | Pro | Val | Ser | Ala | Phe | Thr | Val | Ile | Leu | Ser | Lys | Ala | Tyr | Pro | Ala |
| 1 | | | | 5 | | | | | 10 | | | | | 15 | |
| Val | Gly | Cys | Pro | His | Pro | Ile | Tyr | Glu | Ile | Leu | Tyr | Asn | Arg | Gln | Gln |
| | | | 20 | | | | | 25 | | | | | 30 | | |
| His | Tyr | Asp | Pro | Arg | Ser | Gly | Ile | Phe | Thr | Cys | Lys | Ile | Pro | Gly | Ile |
| | | 35 | | | | | 40 | | | | | 45 | | | |
| Tyr | Tyr | Phe | Ser | Tyr | His | Val | His | Val | Lys | Gly | Thr | His | Val | Trp | Val |
| | 50 | | | | | 55 | | | | | 60 | | | | |
| Gly | Leu | Tyr | Lys | Asn | Gly | Thr | Pro | Thr | Met | Tyr | Thr | Tyr | Asp | Glu | Tyr |
| 65 | | | | | 70 | | | | | 75 | | | | | 80 |
| Ser | Lys | Gly | Tyr | Leu | Asp | Thr | Ala | Ser | Gly | Ser | Ala | Thr | Met | Glu | Leu |
| | | | | 85 | | | | | 90 | | | | | 95 | |
| Thr | Glu | Asn | Asp | Gln | Val | Trp | Leu | Gln | Leu | Pro | Asn | Ala | Glu | Ser | Asn |
| | | | 100 | | | | | 105 | | | | | 110 | | |
| Gly | Leu | Tyr | Ser | Ser | Glu | Tyr | Val | His | Ser | Ser | Phe | Ser | Gly | Phe | Leu |
| | | 115 | | | | | 120 | | | | | 125 | | | |
| Val | Ala | Pro | Met | | | | | | | | | | | | |
| | | | 130 | | | | | | | | | | | | |

( 2 ) INFORMATION FOR SEQ ID NO:6:

( i ) SEQUENCE CHARACTERISTICS:
        ( A ) LENGTH: 1313 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 73..804

( x i ) SEQUENCE DESCRIPTION: SEQ ID NO:6:

AGGTCGACGG TATCGATAAG CTTGATATCG AATTCCGGCT GCGGTTCTGA TTCCATACCA     60

GAGGGGCTCA GG ATG CTG TTG CTG GGA GCT GTT CTA CTG CTA TTA GCT     108

-continued

```
                  Met  Leu  Leu  Leu  Gly  Ala  Val  Leu  Leu  Leu  Leu  Ala
                   1                  5                           10

CTG  CCC  GGT  CAT  GAC  CAG  GAA  ACC  ACG  ACT  CAA  GGG  CCC  GGA  GTC  CTG    156
Leu  Pro  Gly  His  Asp  Gln  Glu  Thr  Thr  Thr  Gln  Gly  Pro  Gly  Val  Leu
          15                      20                      25

CTT  CCC  CTG  CCC  AAG  GGG  GCC  TGC  ACA  GGC  TGG  ATG  GCG  GGC  ATC  CCA    204
Leu  Pro  Leu  Pro  Lys  Gly  Ala  Cys  Thr  Gly  Trp  Met  Ala  Gly  Ile  Pro
          30                      35                      40

GGG  CAT  CCG  GGC  CAT  AAT  GGG  GCC  CCA  GGC  CGT  GAT  GGC  AGA  GAT  GGC    252
Gly  His  Pro  Gly  His  Asn  Gly  Ala  Pro  Gly  Arg  Asp  Gly  Arg  Asp  Gly
 45                      50                      55                      60

ACC  CCT  GGT  GAG  AAG  GGT  GAG  AAA  GGA  GAT  CCA  GGT  CTT  ATT  GGT  CCT    300
Thr  Pro  Gly  Glu  Lys  Gly  Glu  Lys  Gly  Asp  Pro  Gly  Leu  Ile  Gly  Pro
                         65                      70                      75

AAG  GGA  GAC  ATC  GGT  GAA  ACC  GGA  GTA  CCC  GGG  GCT  GAA  GGT  CCC  CGA    348
Lys  Gly  Asp  Ile  Gly  Glu  Thr  Gly  Val  Pro  Gly  Ala  Glu  Gly  Pro  Arg
                80                      85                      90

GGC  TTT  CCG  GGA  ATC  CAA  GGC  AGG  AAA  GGA  GAA  CCT  GGA  GAA  GGT  GCC    396
Gly  Phe  Pro  Gly  Ile  Gln  Gly  Arg  Lys  Gly  Glu  Pro  Gly  Glu  Gly  Ala
                95                      100                     105

TAT  GTA  TAC  CGC  TCA  GCA  TTC  AGT  GTG  GGA  TTG  GAG  ACT  TAC  GTT  ACT    444
Tyr  Val  Tyr  Arg  Ser  Ala  Phe  Ser  Val  Gly  Leu  Glu  Thr  Tyr  Val  Thr
110                      115                     120

ATC  CCC  AAC  ATG  CCC  ATT  CGC  TTT  ACC  AAG  ATC  TTC  TAC  AAT  CAG  CAA    492
Ile  Pro  Asn  Met  Pro  Ile  Arg  Phe  Thr  Lys  Ile  Phe  Tyr  Asn  Gln  Gln
125                      130                     135                     140

AAC  CAC  TAT  GAT  GGC  TCC  ACT  GGT  AAA  TTC  CAC  TGC  AAC  ATT  CCT  GGG    540
Asn  His  Tyr  Asp  Gly  Ser  Thr  Gly  Lys  Phe  His  Cys  Asn  Ile  Pro  Gly
                         145                     150                     155

CTG  TAC  TAC  TTT  GCC  TAC  CAC  ATC  ACA  GTC  TAT  ATG  AAG  GAT  GTG  AAG    588
Leu  Tyr  Tyr  Phe  Ala  Tyr  His  Ile  Thr  Val  Tyr  Met  Lys  Asp  Val  Lys
                160                     165                     170

GTC  AGC  CTC  TTC  AAG  AAG  GAC  AAG  GCT  ATG  CTC  TTC  ACC  TAT  GAT  CAG    636
Val  Ser  Leu  Phe  Lys  Lys  Asp  Lys  Ala  Met  Leu  Phe  Thr  Tyr  Asp  Gln
          175                     180                     185

TAC  CAG  GAA  AAT  AAT  GTG  GAC  CAG  GCC  TCC  GGC  TCT  GTG  CTC  CTG  CAT    684
Tyr  Gln  Glu  Asn  Asn  Val  Asp  Gln  Ala  Ser  Gly  Ser  Val  Leu  Leu  His
190                      195                     200

CTG  GAG  GTG  GGC  GAC  CAA  GTC  TGG  CTC  CAG  GTG  TAT  GGG  GAA  GGA  GAG    732
Leu  Glu  Val  Gly  Asp  Gln  Val  Trp  Leu  Gln  Val  Tyr  Gly  Glu  Gly  Glu
205                      210                     215                     220

CGT  AAT  GGA  CTC  TAT  GCT  GAT  AAT  GAC  AAT  GAC  TCC  ACC  TTC  ACA  GGC    780
Arg  Asn  Gly  Leu  Tyr  Ala  Asp  Asn  Asp  Asn  Asp  Ser  Thr  Phe  Thr  Gly
                225                     230                     235

TTT  CTT  CTC  TAC  CAT  GAC  ACC  AAC  TGATCACCAC TAACTCAGAG CCTCCTCCAG           834
Phe  Leu  Leu  Tyr  His  Asp  Thr  Asn
                240

GCCAAACAGC CCCAAAGTCA ATTAAAGGCT TTCAGTACGG TTAGGAAGTT GATTATTATT                  894

TAGTTGGAGG CCTTTAGATA TTATTCATTC ATTTACTCAT TCATTTATTC ATTCATTCAT                  954

CAAGTAACTT TAAAAAAATC ATATGCTATG TTCCCAGTCC TGGGGAGCTT CACAAACATG                 1014

ACCAGATAAC TGACTAGAAA GAAGTAGTTG ACAGTGCTAT TTCGTGCCCA CTGTCTCTCC                 1074

TGATGCTCAT ATCAATCCTA TAAGGCACAG GGAACAAGCA TTCTCCTGTT TTTACAGATT                 1134

GTATCCTGAG GCTGAGAGAG TTAAGTGAAT GTCTAAGGTC ACACAGTATT AAGTGACAGT                 1194

GCTAGAAATC AAACCCAGAG CTGTGGACTT TGTTCACTAG ACTGTGCCCC TTTTATAGAG                 1254

GGTACATGTT CTCTTTGGAG TGTTGGTAGG TGTCTGTTTC CCACCTCACC TGAGAGCCA                  1313
```

(2) INFORMATION FOR SEQ ID NO:7:

(i) SEQUENCE CHARACTERISTICS:
        (A) LENGTH: 244 amino acids
        (B) TYPE: amino acid
        (D) TOPOLOGY: linear (ii) MOLECULE TYPE: protein (xi) SEQUENCE DESCRIPTION: SEQ ID NO:7:

```
Met Leu Leu Leu Gly Ala Val Leu Leu Leu Leu Ala Leu Pro Gly His
 1               5                  10                  15
Asp Gln Glu Thr Thr Thr Gln Gly Pro Gly Val Leu Leu Pro Leu Pro
            20                  25                  30
Lys Gly Ala Cys Thr Gly Trp Met Ala Gly Ile Pro Gly His Pro Gly
        35                  40                  45
His Asn Gly Ala Pro Gly Arg Asp Gly Arg Asp Gly Thr Pro Gly Glu
    50                  55                  60
Lys Gly Glu Lys Gly Asp Pro Gly Leu Ile Gly Pro Lys Gly Asp Ile
65                  70                  75                  80
Gly Glu Thr Gly Val Pro Gly Ala Glu Gly Pro Arg Gly Phe Pro Gly
                85                  90                  95
Ile Gln Gly Arg Lys Gly Glu Pro Gly Glu Gly Ala Tyr Val Tyr Arg
            100                 105                 110
Ser Ala Phe Ser Val Gly Leu Glu Thr Tyr Val Thr Ile Pro Asn Met
        115                 120                 125
Pro Ile Arg Phe Thr Lys Ile Phe Tyr Asn Gln Gln Asn His Tyr Asp
    130                 135                 140
Gly Ser Thr Gly Lys Phe His Cys Asn Ile Pro Gly Leu Tyr Tyr Phe
145                 150                 155                 160
Ala Tyr His Ile Thr Val Tyr Met Lys Asp Val Lys Val Ser Leu Phe
                165                 170                 175
Lys Lys Asp Lys Ala Met Leu Phe Thr Tyr Asp Gln Tyr Gln Glu Asn
            180                 185                 190
Asn Val Asp Gln Ala Ser Gly Ser Val Leu Leu His Leu Glu Val Gly
        195                 200                 205
Asp Gln Val Trp Leu Gln Val Tyr Gly Glu Gly Glu Arg Asn Gly Leu
    210                 215                 220
Tyr Ala Asp Asn Asp Asn Asp Ser Thr Phe Thr Gly Phe Leu Leu Tyr
225                 230                 235                 240
His Asp Thr Asn
```